United States Patent [19]

Moodley

[11] Patent Number: 5,632,621
[45] Date of Patent: May 27, 1997

[54] DENTURES FOR ANTERIOR TEETH

[76] Inventor: Sundru M. Moodley, 610 S. Harrison La., Denver, Colo. 80209

[21] Appl. No.: 516,027

[22] Filed: Aug. 17, 1995

[51] Int. Cl.$^6$ ................................................ A61C 13/10
[52] U.S. Cl. ........................................................ 433/192
[58] Field of Search ............................ 433/191, 192 OR, 433/193, 194, 195

[56] References Cited

U.S. PATENT DOCUMENTS

| | | | |
|---|---|---|---|
| 200,284 | 2/1878 | Hall | 433/192 |
| 350,871 | 10/1886 | Curtis | 433/192 |
| 440,131 | 11/1890 | Brewster | 433/192 |
| 461,844 | 10/1891 | Payne | 433/192 |
| 638,019 | 11/1899 | Justi | 433/192 |
| 1,209,142 | 12/1916 | Glenn | 433/192 |
| 1,241,854 | 10/1917 | Justi | 433/192 |
| 1,384,282 | 7/1921 | Tuttle | 433/192 |
| 2,301,825 | 11/1942 | Stein et al. | 433/192 |
| 2,328,379 | 8/1943 | Erdle | 433/192 |
| 2,370,488 | 2/1945 | Raber | 433/192 |
| 2,419,084 | 4/1947 | Myerson et al. | 433/191 |
| 2,600,496 | 6/1952 | Hall | 433/192 |
| 3,327,392 | 6/1967 | Crow | 433/192 |
| 3,423,831 | 1/1969 | Semmelman | 433/191 |
| 3,785,054 | 1/1974 | Van Handel | 433/168.1 |
| 4,608,020 | 8/1986 | Laszlo | 433/213 |

FOREIGN PATENT DOCUMENTS

| | | |
|---|---|---|
| 592388 | 8/1925 | France . |
| 620397 | 4/1927 | France . |
| 360002 | 9/1922 | Germany . |
| 10211 | of 1891 | United Kingdom . |
| 5474 | of 1911 | United Kingdom . |
| 245054 | 2/1926 | United Kingdom . |
| 291464 | 6/1928 | United Kingdom . |

*Primary Examiner*—John J. Wilson
*Attorney, Agent, or Firm*—Carol W. Burton

[57] ABSTRACT

A denture of the present invention includes a molded, plastic dental plate in which is mounted at least one anterior artificial tooth. The anterior artificial tooth includes a base surface and a concealed portion which are mounted in a base portion of the dental plate. The anterior artificial tooth also includes an incisal edge, a lingual surface and a buccal surface. Formed in the interior of the anterior artificial tooth is a passageway substantially elliptical in cross section which extends vertically from the base surface to the lingual surface, spaced apart from the incisal edge. The material from which the dental plate is manufactured extends from the base of the dental plate through the passageway and extends one lingual surface of the anterior artificial tooth, to form an integral dental plate base, column and lingual coating. The coating extends contiguously over the lingual surface of adjacent anterior artificial teeth. A method of manufacturing the improved denture of the present invention is also disclosed.

3 Claims, 2 Drawing Sheets

DENTURES FOR ANTERIOR TEETH

FIELD OF THE INVENTION

This invention relates to dentures and more particularly to new and improved upper and lower dentures for anterior teeth.

BACKGROUND OF THE INVENTION

Dentures are conventionally made by insertion of acrylic or porcelain artificial teeth into a molded plastic dental plate base. The teeth are inserted into the dental plate when the dental plate is in a molten state, so that as the dental plate cools and/or cures, the artificial teeth become fixedly mounted in the dental plate. The dental plate material is conventionally made of a flesh-colored plastic so as to resemble natural gums, and the artificial teeth are conventionally made of an off-white plastic so as to resemble natural teeth.

Artificial teeth are subject to significant mastication forces. Over time, these forces tend to loosen artificial teeth from their attachment in the dental plate in which they are mounted. Eventually, artificial teeth may pop out of the dental plate. Such displacement can cause substantial embarrassment to the denture wearer, who is further inconvenienced by the cost and time required for denture repair.

To prevent such loosening, an adhesive is sometimes applied between the artificial teeth and the dental plate material in which the teeth are mounted. In addition, artificial teeth may be formed with a slightly enlarged mid-section which is positioned just below the natural "gum line" of the dental plate. When such artificial teeth are mounted in the dental plate, the dental plate extends slightly over the enlarged mid-section to form a "gum line" rim or flange which helps maintain the artificial teeth in the dental plate. Because, however, this "gum line" rim of dental plate material typically extends over the enlarged mid-section of artificial teeth only to ½ millimeter, the rim may not have sufficient strength to counteract the repeated mastication forces to which the artificial teeth are subject. Eventually, the "gum line" rim of dental plate material may break, allowing the artificial tooth over which it extended to become displaced from dental plate in which it is mounted.

In an attempt to further secure artificial teeth in dentures, cavities are sometimes formed in artificial teeth. Such cavities may extend from the base of an artificial teeth into the interior of the artificial tooth. When an artificial tooth is so constructed, during denture assembly molten denture plate material flows into the cavity formed in the artificial tooth, thereby extending a portion of the dental plate into the artificial tooth. While this construction does increase the surface area of contact between the denture plate and the artificial tooth, the artificial tooth may still exhibit a tendency to slip out of the denture plate after experiencing the repeated stress of mastication.

When artificial teeth fall out of a dental plate, the denture and loose artificial tooth must be repaired. Naturally, the repair process creates significant inconvenience to the denture wearer. If a "gum line" rim is broken, the repaired denture may appear flawed. Moreover, if the portion of the denture plate which extends into the core of an artificial tooth has been broken, the repaired denture may be unable to withstand mastication forces as well as the original denture.

It is against this background that the significant improvements and advancement of the present invention have taken place in the field of dentures.

SUMMARY OF THE INVENTION

In accordance with its major aspects, dentures of the present invention comprise at least one anterior artificial tooth mounted in a denture plate base. The artificial anterior tooth contains a substantially vertical passageway formed therein extending from a base of the tooth to an opening formed in the lingual surface of the tooth. The passageway is substantially elliptical in cross section, having a width along an axis substantially parallel to the buccal surface of the tooth which is greater than the diameter of the passageway transverse to said axis. Dental plate material extends from the denture base up through the passageway to form a column also having a substantially elliptical cross section. Dental plate material also extends over a portion of the lingual surface of the tooth to form a lingual coating which is integral with the denture base. An exposed lingual surface of the tooth is maintained between the incisal edge of the tooth and the opening in the lingual surface. An interproximal space formed between adjacent anterior artificial teeth of the present invention is partially covered with the lingual coating, thereby making the lingual coating contiguous over adjacent anterior artificial teeth of the present invention.

The present invention provides for dentures having securely fitting anterior artificial teeth. As a result, time and costs required for denture repair sessions when artificial anterior teeth become displaced from the denture in which they were mounted is minimized.

A more complete appreciation of the present invention and its scope can be obtained from understanding the accompanying drawings which are briefly summarized below, the following detailed description of the presently preferred embodiment of the present invention, and the appended claims.

DETAILED DESCRIPTION

Figure 1:
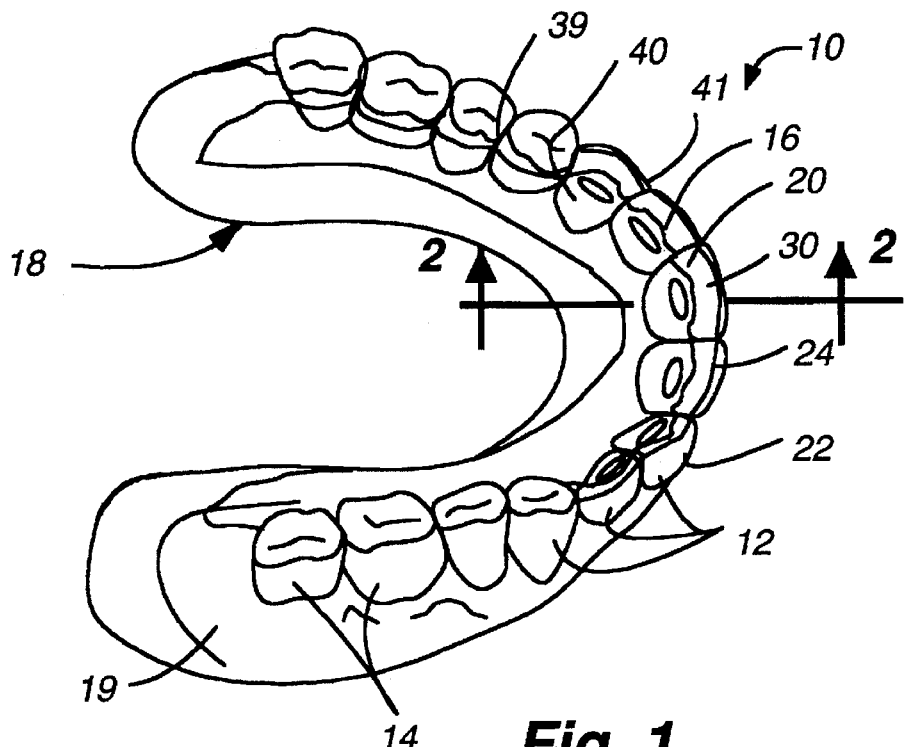
FIG. 1 is a perspective view of an improved lower denture which includes six anterior artificial teeth and incorporates the present invention.

One embodiment of an improved denture 10 in which anterior artificial teeth exhibit increased security and stability is shown in FIGS. 1 through 5. The denture 10 includes a plurality of artificial teeth 12. The artificial teeth 12 include posterior artificial teeth 14 and anterior artificial teeth 16. In the full mouth lower denture 10, just as in a full mouth upper denture (not shown), there are typically six anterior artificial teeth 16. The denture 10 includes a dental plate 18 which is preferably constructed of an acrylic, most preferably a methylmethacrylate, and is tinted a flesh color to resemble the natural gums of the denture wearer. The artificial teeth 12 are embedded in a base portion 19 of the dental plate 18 during the assembly process.

An anterior artificial tooth 16 of the present invention includes a lingual surface 20, having a concave surface 21 closely resembling the natural lingual contour of real teeth, an opposing buccal surface 22, an incisal edge 24, a base surface 26, a concealed lingual portion 28, and an exposed lingual portion 30 adjacent the incisal edge 24. Formed in the anterior artificial tooth 16 is a substantially vertical passageway 32 which extends from a base opening 34 formed in the base surface 26 of the tooth 16, to a lingual opening 36 formed in the lingual surface 20 of the tooth 16. The passageway 32 is substantially elliptical in cross section, having a width "w" which is greater in length than a diameter "d" thereof. The lingual opening 36 is also elliptical in cross section, and is positioned spaced apart from the incisal edge 24 and adjacent the exposed lingual portion 30.

Figure 2:
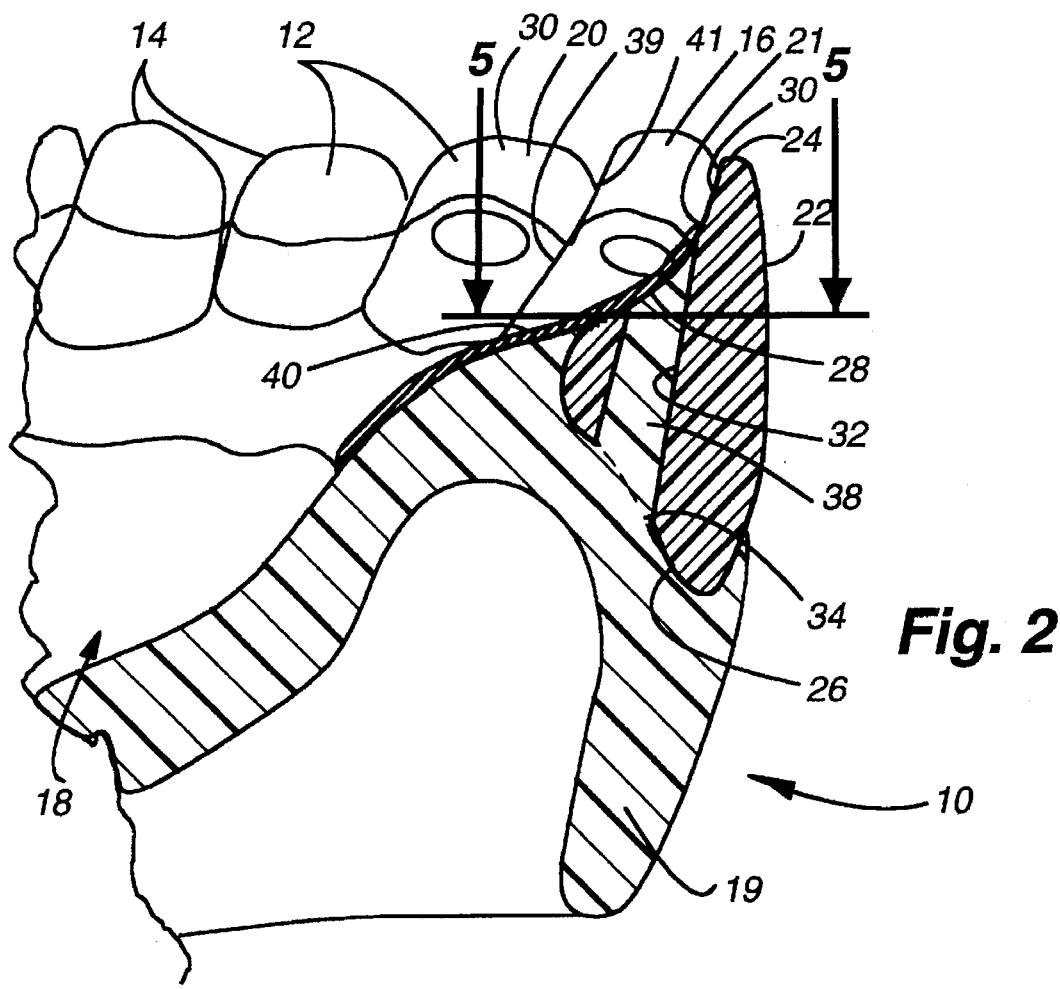
FIG. 2 is a elevation section view of the lower denture shown in FIG. 1 taken substantially along the line 2—2 of FIG. 1.
Figure 3:
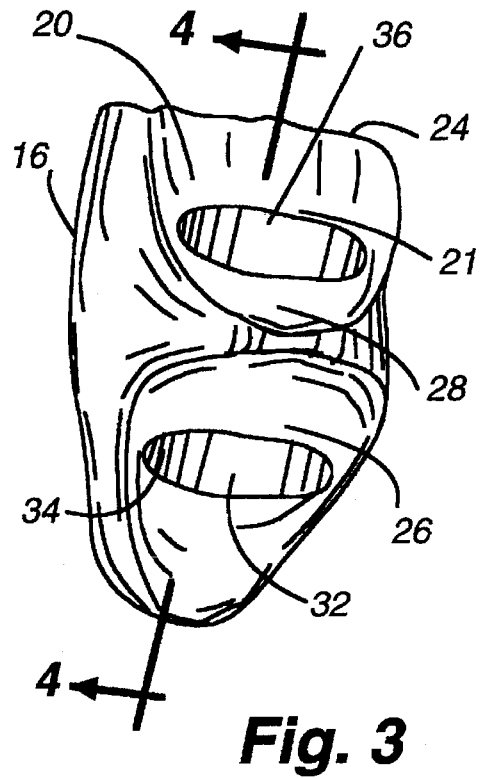
FIG. 3 is a perspective view of the artificial tooth shown in FIG. 2 apart from the dental plate in which it is otherwise mounted.
Figure 5:
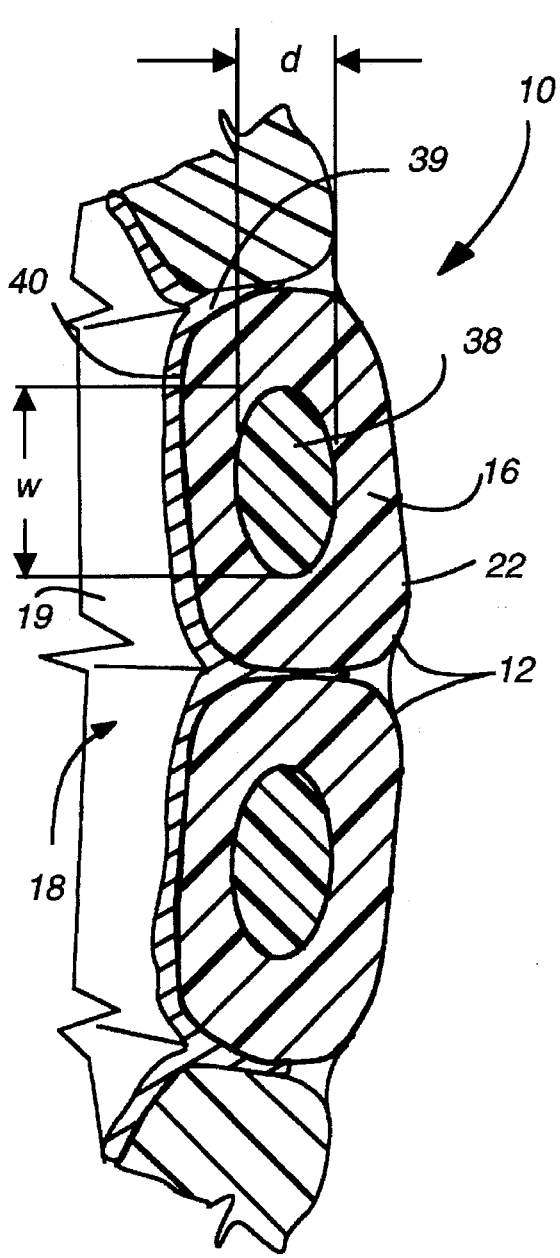
FIG. 5 is a section view of the anterior artificial tooth shown in FIG. 2 taken substantially along the line 5—5 of FIG. 2.
Figure 4:
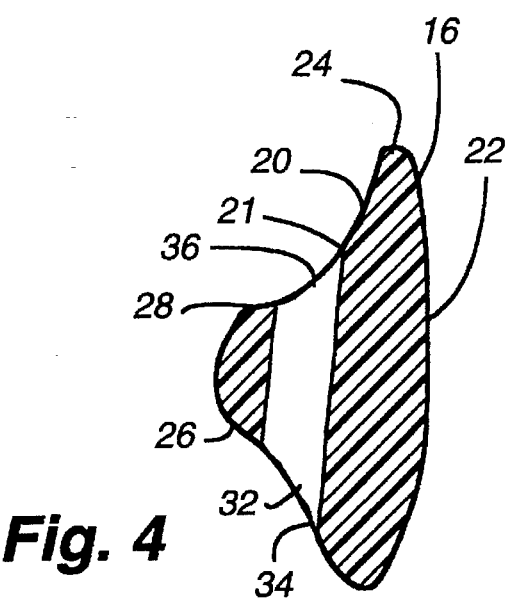
FIG. 4 is a section view of the anterior artificial tooth shown in FIG. 3 taken substantially along the line 4—4 of FIG. 3.

Referring now to FIG. 2, when an anterior artificial tooth 16 is mounted in the dental plate 18, dental plate material extends into the passageway 32 of the artificial tooth 16 to form a column 38 of dental plate material. The column 38 is substantially elliptical in cross section, in substantial conformance with the shape and dimensions "w" and "d" of the passageway 32.

Dental plate material also extends over the concealed lingual portion 28 of the lingual surface 20 to form a lingual coating 40. The lingual coating 40 is contiguous between adjacent anterior artificial teeth 16, extending over and covering a lingual portion 39 of the anterior interproximal spaces 41 formed between adjacent anterior artificial teeth 16.

The lingual coating 40 is preferably approximately ½ to 1 millimeter thick, with the naturally concave surface 21 of the lingual surface 20 of the anterior artificial teeth 16 substantially maintained. The lingual coating 40 forms an integral mass with the column 38 and the base portion 19, which collectively constitute the dental plate 18.

In the preferred embodiment, the exposed lingual portion 30 extends approximately 1–3 millimeters from the incisal edge 24 to just adjacent the lingual opening 36. By maintaining a lingual coating 40 of less than or equal to 1 millimeter in thickness and keeping the exposed lingual portion 30 substantially free of dental plate material, the lingual coating 40 is substantially translucent over the concealed lingual portion 28 of the lingual surface 20 and is not readily visible to others, giving the denture 10 a more natural appearance.

The anterior artificial teeth 16 of the present invention are preferably manufactured according to conventional molding techniques, except that after an individual tooth 16 is formed, the tooth 16 is drilled to form the passageway 32. Alternatively, the passageway 32 may be formed in the tooth 16 when the tooth 16 is originally molded.

To assemble the improved denture 10 of the present invention, a negative impression is made of the denture wearer's gum. Using plaster, a positive impression is then made based on the negative impression. The positive impression is covered with a sheet of wax which is 2–3 mm thick. The anterior artificial teeth 16 of the present invention are mounted in the wax. Wax is applied to the passageway 32 and onto a portion of the lingual surface 20 of the teeth 16. The positive impression, together with the wax and teeth 16, are placed in a first half of a mold which is partially filled with plaster. The wax and teeth 16 are covered with a separating medium and the second half of the mold is joined to the first half. The mold is capped and the wax removed by boiling. The mold is filled under pressure with liquid acrylic, which replaces the previously waxed portions with acrylic material. The acrylic is cured under heat. The plaster is removed after heating, with the anterior artificial teeth embedded in the acrylic dental plate 18 and the acrylic dental plate material extending to form the column 38, the lingual coating 40 and to cover portions of the anterior interproximal spaces 41.

Because the dental plate 18 of the present invention includes dental plate material which extends to form an integral mass surrounding the concealed portion 28 of each anterior artificial tooth 16, extending into the interior passageway 32 of each such tooth, substantially covering a portion of the lingual surface 20 of each such tooth, and is contiguous between adjacent anterior artificial teeth 16, each anterior artificial tooth 16 of the present invention is strongly secured in the dental plate 18. The elliptical cross section of each column 38 prevents anterior artificial tooth 16 from becoming loose and rotating about the column 38 which extends therethrough. The elliptical cross section of the column 38 also provides an increased surface area of contact for attachment between the column 38 and the passageway 32, as compared to a smaller cylindrical column, circular in cross section. All of these features contribute to prevent displacement of anterior artificial teeth 16 from the dental plate 18. Need for repairs to the denture 10 is thereby minimized, and the concomitant risk that the denture wearer will be without dentures is thereby lessened.

Presently preferred embodiments of the present invention and many improvements have been described with a degree of particularity. It should be understood that the present invention is defined by the spirit and scope of the following claims.

I claim:

1. An improved denture, comprising:
   at least one anterior artificial tooth having a base surface, an incisal edge, a lingual surface, and a buccal surface, said anterior artificial tooth defining a substantially vertical passageway having a substantially elliptical cross section and extending substantially parallel to said buccal surface from said base surface to intersect said lingual surface at a position adjacent to but spaced from said incisal edge; and
   a molded denture plate of dental plate material, wherein said artificial tooth is mounted in said denture plate, said dental plate material integrally extends through said passageway and covers a portion of said lingual surface of said artificial tooth, with at least a portion of said dental plate material covering said portion of said lingual surface in a thickness of approximately 1 millimeter, thereby securely maintaining said artificial tooth in said denture plate.

2. An improved denture, comprising:
   at least one anterior artificial tooth having a base surface, an incisal edge, a lingual surface, and a buccal surface, said anterior artificial tooth defining a substantially vertical passageway having a substantially elliptical cross section and extending substantially parallel to said buccal surface from said base surface to intersect said lingual surface at a position adjacent to but spaced from said incisal edge; and
   a molded denture plate of dental plate material, wherein said artificial tooth is mounted in said denture plate, said dental plate material integrally extends through said passageway and covers said lingual surface, wherein said dental plate material covering said lingual surface extends to within from 1 to 3 millimeters of said incisal edge and is from approximately ½ to 1 millimeter thick.

3. An improved denture, comprising:

a dental plate molded of acrylic material; and a plurality of adjacent anterior artificial teeth, each said tooth having a base portion mounted in said denture plate and extending outwardly therefrom, each said anterior artificial tooth further having a base surface, an incisal edge, a lingual surface, an exposed lingual portion, and a buccal surface, each said artificial tooth defining a substantially vertical passageway having a width "w" substantially parallel to said buccal surface and substantially greater in length than a diameter "d", and extending from said base surface substantially parallel to said buccal surface and opening into said lingual surface at a position adjacent to said exposed lingual portion and spaced from said incisal edge, said acrylic material integrally extending through said passageway, substantially covering said lingual surface except said exposed lingual portion and extending contiguously between adjacent artificial anterior teeth, with said acrylic material having a thickness of approximately ½ to 1 millimeters adjacent said exposed lingual portion, thereby securely maintaining said anterior artificial teeth in said denture plate.

* * * * *